United States Patent
Tsai et al.

(10) Patent No.: US 12,419,532 B2
(45) Date of Patent: Sep. 23, 2025

(54) METHOD OF EVALUATING CORE MUSCLES BY BIOIMPEDANCE TECHNOLOGY

(71) Applicant: CHARDER ELECTRONIC CO., LTD., Taichung (TW)

(72) Inventors: Chuan-Chung Tsai, Taichung (TW); Kuen-Chang Hsieh, Taichung (TW)

(73) Assignee: CHARDER ELECTRONIC CO., LTD., Taichung (TW)

( * ) Notice: Subject to any disclaimer, the term of this patent is extended or adjusted under 35 U.S.C. 154(b) by 731 days.

(21) Appl. No.: 17/825,881

(22) Filed: May 26, 2022

(65) Prior Publication Data

US 2023/0320607 A1 Oct. 12, 2023

(30) Foreign Application Priority Data

Apr. 6, 2022 (TW) .................................. 111113094

(51) Int. Cl.
*A61B 5/053* (2021.01)

(52) U.S. Cl.
CPC .......... *A61B 5/053* (2013.01); *A63B 2225/50* (2013.01); *A63B 2230/08* (2013.01)

(58) Field of Classification Search
CPC ....... A61B 5/053; A61B 5/4519; A61B 5/107; A63B 2225/50; A63B 2230/08
See application file for complete search history.

(56) References Cited

U.S. PATENT DOCUMENTS

| | | | | |
|---|---|---|---|---|
| 2004/0167423 A1* | 8/2004 | Pillon | ................. | A61B 5/7445 |
| | | | | 600/547 |
| 2011/0112428 A1* | 5/2011 | Hsieh | .................. | A61B 5/7264 |
| | | | | 600/547 |
| 2016/0157749 A1* | 6/2016 | Bohorquez | ......... | A61B 5/4872 |
| | | | | 600/393 |
| 2019/0343459 A1* | 11/2019 | Korzinov | .............. | A61B 5/316 |

* cited by examiner

*Primary Examiner* — May A Abouelela
*Assistant Examiner* — Yasmeen S Warsi
(74) *Attorney, Agent, or Firm* — Muncy, Geissler, Olds & Lowe, P.C.

(57) ABSTRACT

A method of evaluating core muscles by bioimpedance technology, includes the steps of: (a) measuring the resistance and reactance of a subject by a bioimpedance measuring instrument, and obtaining the subject's age, gender, and impedance factor ($h^2/Z$), and (b) calculating the cross-sectional area of the subject's core muscles by the following formula: $BIA = a - b \times age + c \times h^2/Z + d \times Sex$. Thereby, measures the cross-sectional area of the core muscles by bioimpedance analysis. The core muscles can be evaluated by the cross-sectional area of the core muscles, which can effectively reduce the measurement cost, reduce the measurement time and improve the convenience of measurement.

3 Claims, 5 Drawing Sheets a) Measure the resistance and reactance of a subject by a bioimpedance measuring instrument, and obtain the subject's age, gender, and impedance factor($h^2/Z$)

(b) Calculating the subject's core muscles by the following formula: $BIA = a - b \times age + c \times h^2/Z + d \times Sex$

FIG. 1

METHOD OF EVALUATING CORE MUSCLES BY BIOIMPEDANCE TECHNOLOGY

BACKGROUND OF THE INVENTION

1. Field of the Invention

The present invention is related to bioimpedance technology, especially refers to a method of evaluating core muscles by bioimpedance technology.

2. Description of the Related Art

Trunk muscles can provide a key role in maintaining stability and balance during movement of the limbs. A strong and stable torso provides a solid foundation for torque-generating limb movements. Among the muscles located in the trunk, the psoas major (PM) in the core muscles (CM) is the only muscle that connects the lumbar spine with the lower extremities. Therefore, the core muscles obviously play an important role in the motor function of the trunk and limbs.

The cross-sectional area (CSA) of the core muscles is becoming an important indicator of health status by morphometric analysis, and aerobic exercise and resistance training are one of the main ways to increase the cross-sectional area of muscle fibers. In addition, the lateral rotation and abduction of the hip joint are also related to the movement of the core muscles. Therefore, the cross-sectional area of the core muscles has been used in many studies, such as: to predict the overall muscle mass, cardiorespiratory fitness, sarcopenia and postoperative outcomes in elderly patients.

Since muscles can be divided into surface muscles and deep muscles, but deep muscles cannot be measured in contact, only electronic signal processing and imaging techniques can be used to diagnose deep muscles. The core muscles are deep muscles. Numerous studies provide substantial data on core size and anatomical variation. Among them, ultrasonic guidance that is mainly used to measure the position of core muscles, and computed tomography (CT) or magnetic resonance imaging (MRI) in imaging technology that is used to measure core muscles, are the most accurate methods. However, there is still a slight difference in the measurement results of the normal and diseased (calcifications and air bubbles in the abscess) psoas between the two methods. In addition, the measurement methods of computed tomography or magnetic resonance imaging also have shortcomings such as high equipment cost, time-consuming measurement, and inconvenient operation. At present, there is no effective method that can effectively improve these shortcomings.

SUMMARY OF THE INVENTION

The present invention has been accomplished under the circumstances in view. It is the main object of the present invention to provide a method of evaluating core muscles by bioimpedance technology, which uses bioelectrical impedance analysis (BIA) to measure the cross-sectional area of the core muscles, so that the core muscles can be evaluated by the cross-sectional area of the core muscles. Compared with the conventional measurement methods of magnetic resonance imaging or computed tomography, the present invention can effectively reduce the measurement cost, reduce the measurement time, and improve the convenience of measurement.

To achieve this and other objects of the present invention, the present invention provides a method of evaluating core muscles by bioimpedance technology, which comprises the steps of:

(a) measuring the resistance and reactance of a subject by a bioimpedance measuring instrument, and obtaining the subject's age, gender, and impedance factor ($h^2/Z$); and (b) calculating the subject's core muscles by the following formula: $BIA = a - b \times age + c \times h^2/Z + d \times Sex$.

Thereby, in the method of evaluating core muscles by bioimpedance technology provided by the present invention, the bioimpedance value measured by the bioimpedance measuring instrument is used to estimate the cross-sectional area of the subject's core muscles by calculating the formula, which is used as the basis for evaluating the subject's core muscles. Compared with computed tomography or magnetic resonance imaging, it can effectively reduce the measurement cost, reduce the measurement time, and improve the convenience of measurement.

BRIEF DESCRIPTION OF THE DRAWINGS

FIG. 1 is a block diagram of a preferred embodiment of the present invention.

DETAILED DESCRIPTION OF THE INVENTION

Figure 2A:
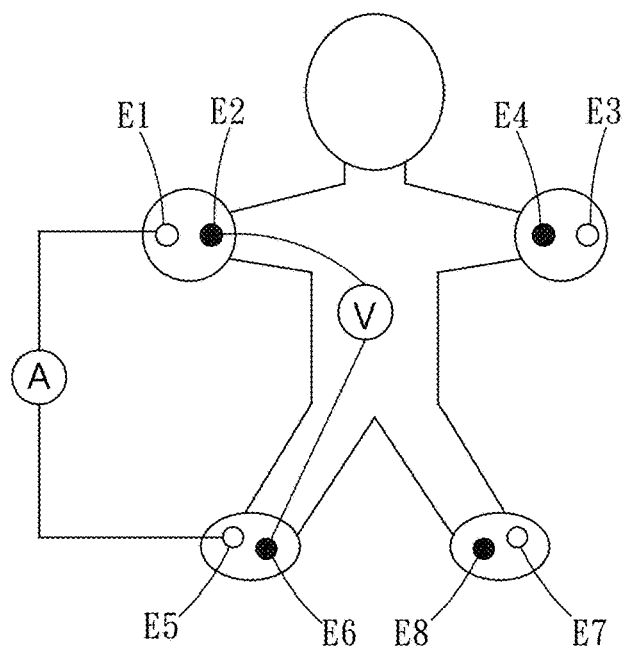
FIGS. 2A-2F are schematic diagrams of measurement modes of a preferred embodiment of the present invention.

In order to explain the technical features of the present invention in detail, the following is a preferred embodiment, and the descriptions are as follows in conjunction with FIGS. 1-3. The method of evaluating core muscles by bioimpedance technology 10, mainly comprises the following steps:

Step (a): Measure the resistance and reactance of a subject by a bioimpedance measuring instrument, and obtain the subject's age, gender, and impedance factor ($h^2/Z$). The bioimpedance measuring instrument is a commonly used instrument in the field of bioimpedance technology, so it is not shown in the drawings. In this preferred embodiment, the bioimpedance measuring instrument is an example of a standing eight-pole plate bioimpedance measuring technology.

Step (b): Calculate the subject's core muscles by the following formula: CM BIA = $a - b \times age + c \times h^2/Z + d \times Sex$ ($r^2 = 0.910$, SEE=13.42 cm$^2$, n=286, p<0.001). In this preferred embodiment, the core muscles comprise psoas major, quadratus muscle (QM), erector spinae(ES), abdominal muscles (AM). The a-d in the calculation formula are the regression coefficients in the regression analysis.

The measurement methods of the present invention can be divided into multiple types, as shown in FIGS. 2A-2F. The left side of the diagram represents the subject's right side, and the right side represents the subject's left side. In the drawings, the current electrodes E1, E3, E5 and E7 of the bioimpedance measuring instrument are represented by hollow circles, and the sensing electrodes E2, E4, E6 and E8 of the bioimpedance measuring instrument are indicated by solid circles.

As shown in FIG. 2A, when the measurement circuit is switched to the current electrodes E1, E5 and the sensing electrodes E2, E6, the impedance value of the right body can be measured.

Figure 2B:
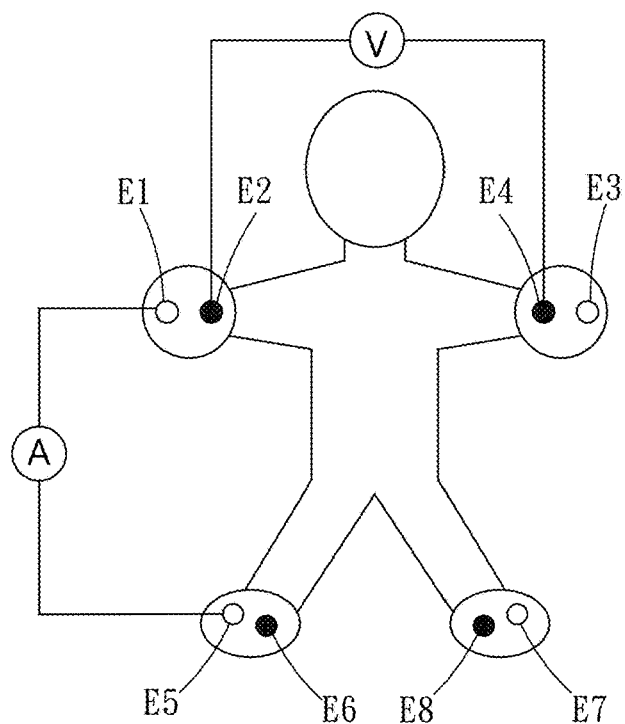

As shown in FIG. 2B, when the measurement circuit is switched to the current electrodes E1, E3 and the sensing electrodes E2, E6, the impedance value of the right upper limb can be measured.

Figure 2C:
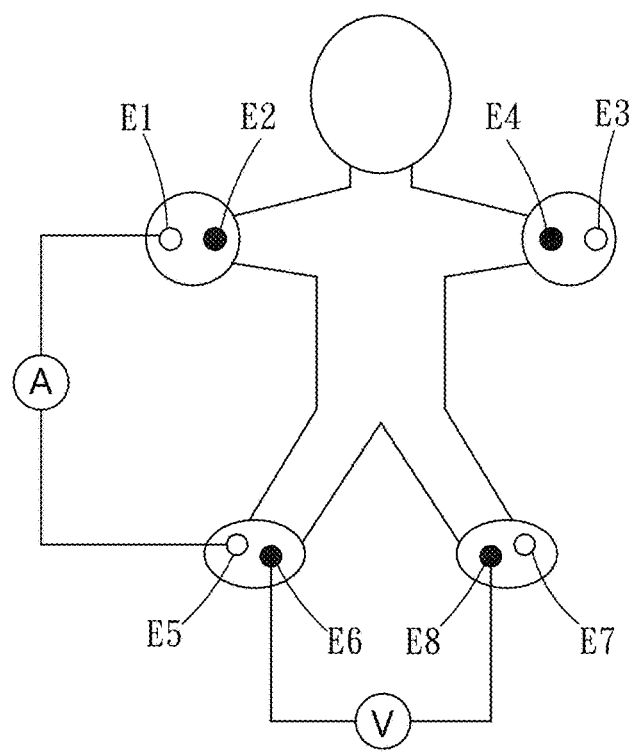

As shown in FIG. 2C, when the measurement circuit is switched to the current electrodes E1, E5, and the sensing electrodes E6, E8, the impedance value of the right lower limb can be measured.

Figure 2D:
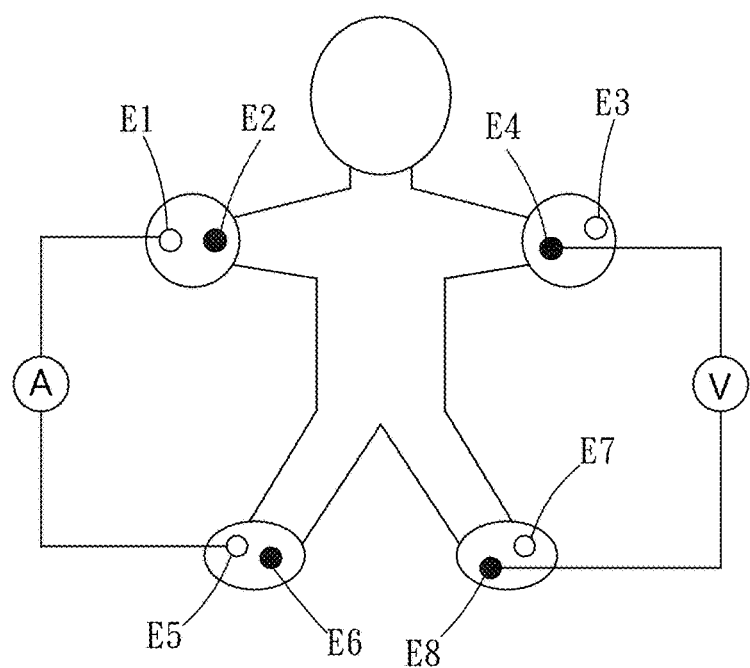

As shown in FIG. 2D, when the measurement circuit switches to the current electrodes E1, E6, and the sensing electrodes E4, E8, the torso impedance value can be measured.

Figure 2E:
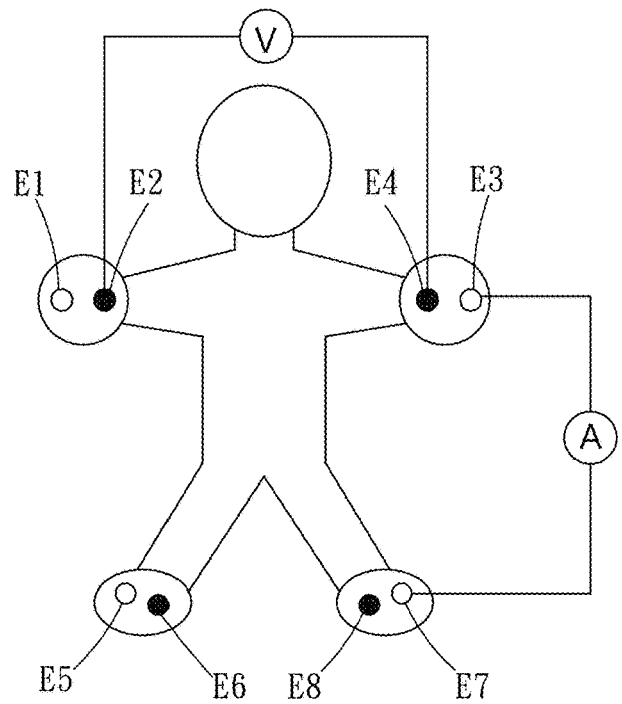

As shown in FIG. 2E, when the measurement circuit switches to the current electrodes E1 and E3, and the sensing electrodes E4 and E8, the impedance value of the left upper limb can be measured.

Figure 2F:
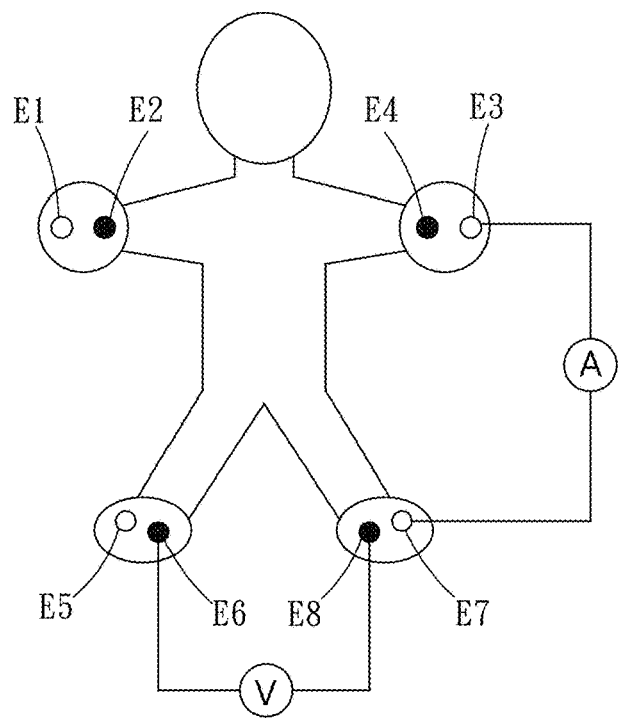

As shown in FIG. 2F, when the measurement circuit is switched to the current electrodes E3, E7, and the sensing electrodes E6, E8, the impedance value of the left lower limb can be measured.

In other preferred embodiments, this core muscles can also be one of psoas major, quadratus lumborum, erector spinae or abdominal muscles, and its calculation formula is:

$$PM_{BIA} = a - b \times age + c \times h^2/Z + d \times Sex (r^2 = 0.919, SEE = 3.31 \; cm^2, n = 286, p < 0.001).$$

$$QM_{BIA} = a - b \times age + c \times h^2/Z + d \times Sex (r^2 = 0.920, SEE = 5.07 \; cm^2, n = 286, p < 0.001).$$

$$ES_{BIA} = a - b \times age + c \times h^2/Z + d \times Sex (r^2 = 0.934, SEE = 13.07 \; cm^2, n = 286, p < 0.001).$$

$$AM_{BIA} = CM_{BIA} - PM_{BIA} - QM_{BIA} - ES_{BIA}.$$

CT Scanning

In this preferred embodiment, the cross-sectional area of the core muscles measured by a computed tomography scanner is used as the estimation target of the present invention. The method of the present invention utilizes variables such as body parameter measurement and bioimpedance measurement of the subject measured by the bioimpedance measuring instrument as predictive variables to establish and verify the estimation model of the cross-sectional area of the core muscles. In other preferred embodiments, the cross-sectional area of the core muscles measured by magnetic resonance imaging can also be used as the estimation target of the present invention.

In this preferred embodiment, a 64-slice computed tomography scan (Somatom Sensation 64 CT system, Siemens Corp., Germany) is performed on the abdomen of each subject, and the data is analyzed using Syngo CT2005A software. Each subject measured the abdominal segment of 2-5 lumbar vertebrae with a computed tomography scanner, but not limited to this.

Image Analysis

Figure 3A:
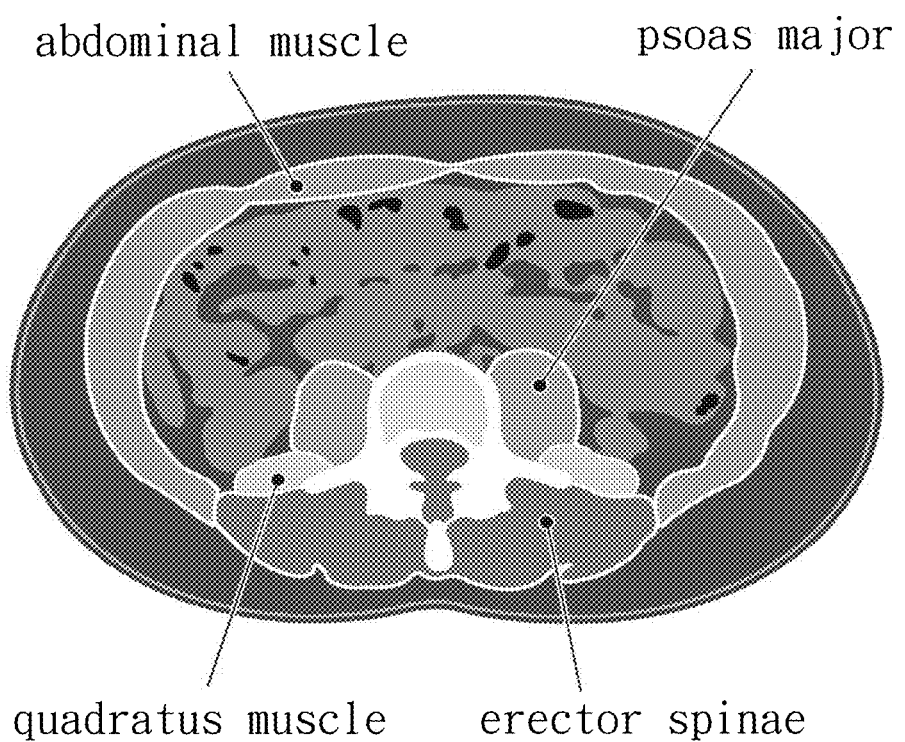
FIG. 3A is a schematic diagram of the abdomen and lean muscle cross-sectional area at the L3-L4 lumbar vertebra height of a preferred embodiment of the present invention.
Figure 3B:
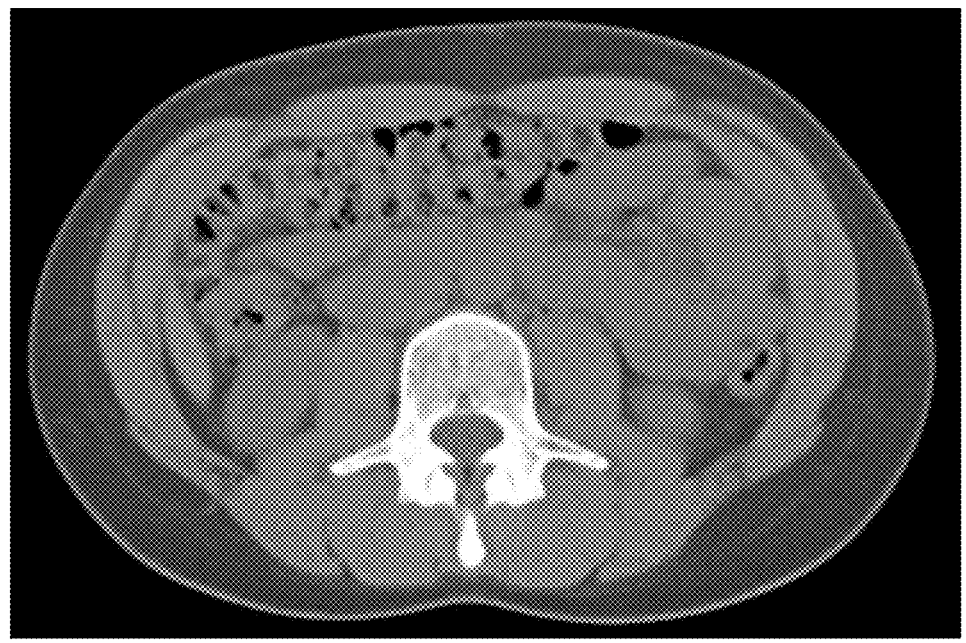
FIG. 3B is a computed tomography image of the abdomen and lean muscle cross-sectional area at the L3-L4 lumbar vertebra height of a preferred embodiment of the present invention.

As shown in FIGS. 3A and 3B, in this preferred embodiment, a fixed image analysis program is used to calculate the abdominal and lean muscle cross section area (CSA) of each subject's L3-L4 lumbar vertebrae heights (in this preferred embodiment, only one computed tomography image is taken for illustration). Image analysts applied Slice-O-Matic version 4.3 software (Tomovision) to circle lean tissue and calculate the circled area. The cross-sectional area of the psoas major and the abdomen is manually divided at the waist L3-L4. In this preferred embodiment, the representative value of the cross-sectional area of the core muscles is the sum of the cross-sectional areas of the psoas major, quadratus lumborum, erector spinae or abdominal muscles. Since the psoas major has a high correlation with height, the values of the psoas major and height are expressed as CSA ($cm^2$) and CSA/height$^2$ ($mm^2/m^2$), respectively.

Statistical Analysis

In this preferred embodiment, as shown in Table 1, the descriptive data are represented by the mean and standard deviation, and their ranges are displayed.

The Student's t-test was used to compare the distribution types, and the Kolmogorov-Smirnov test was used to test the normal distribution of the data. All statistical analyses were performed using SPSS Ver.20 (Statistical Package for the Social Sciences, IBM SPSS statistics for Windows, Armonk, NY: IBM Corp), and the significance level was set at $p<0.05$ (two-tailed). Spearman correlation coefficient analysis was used to describe the correlation between variables, and stepwise regression analysis was used to analyze the relationship between gender, age, impedance factor and the core muscles, psoas, abdominal muscles, quadratus lumborum, erector spinae and area.

TABLE 1

| Items | Female (n = 146) | | Male (n = 140) | | P |
|---|---|---|---|---|---|
| | mean ± SD | Range | mean ± SD | Range | |
| Age (years) | 32.1 ± 16.5 | 18.5-74.8 | 33.8 ± 14.4 | 18.5-77.0 | >0.05 |
| Height (cm) | 160.3 ± 6.4 | 145.0-178.0 | 170.8 ± 5.9 | 151.5-186.0 | <0.01 |
| Weight (kg) | 59.7 ± 10.9 | 42.0-105.0 | 73.9 ± 12.9 | 47.0-120.0 | <0.001 |
| BMI (kg/m$^2$) | 23.2 ± 4.1 | 16.2-38.0 | 25.3 ± 4.0 | 18.2-39.9 | <0.01 |
| Waist (cm) | 81.6 ± 11.2 | 63.0-122.0 | 83.3 ± 10.7 | 64.0-122.0 | <0.05 |
| Hip (cm) | 98.8 ± 9.8 | 81.0-129.0 | 98.9 ± 7.4 | 80.0-122.0 | >0.05 |
| WHR | 0.83 ± 0.06 | 0.71-1.08 | 0.84 ± 0.07 | 0.72-1.03 | <0.05 |
| Bioimpedance | | | | | |
| Z (Ω) | 658.5 ± 89.4 | 421.7-892.3 | 515.3 ± 62.8 | 372.0-668.0 | <0.01 |
| CT | | | | | |
| $CM_{CT}$ (cm$^2$) | 121.6 ± 28.8 | 53.6-209.6 | 217.6 ± 44.8 | 112.0-350.4 | <0.01 |
| $ACSA_{CT}$ (cm$^2$) | 450.7 ± 120.2 | 293.2-988.9 | 499.0 ± 131.8 | 309.7-1026.4 | <0.01 | where, mean±SD (Standard Deviation) is the mean value, and the standard deviation; WHR is waist-hip ratio; BMI is the body mass index; CM is the core muscles; ACSA is the abdominal cross-sectional area.

Thereby, a method of evaluating core muscles by bioimpedance technology 10 provided by the present invention can use the bioimpedance value measured by the bioimpedance measuring instrument without the need for computed tomography or magnetic resonance imaging, and estimate the cross-sectional area of the subject's core muscles by the calculation formula, which is used as the basis for evaluating the subject's core muscles. Compared with computed tomography or magnetic resonance imaging, it can effectively reduce the measurement cost, reduce the measurement time, and improve the convenience of measurement.

The above-mentioned preferred embodiments are intended to help understand the principles and methods of the present invention, and the present invention is not limited to the above-mentioned preferred embodiments. Any combination and modification within the spirit and principle of the present invention shall fall within the protection scope of the present invention.

What is claimed is:

1. A method of evaluating core muscles by bioimpedance technology, comprising the steps of:
    (a) attaching a plurality of electrode sets on hands and feet of a subject in a way that two of the plurality of electrode sets attaching the hands or the feet of the subject to form a measurement loop, measuring and obtaining a resistance and a reactance of the subject by the plurality of electrode sets of a bioimpedance measuring instrument, and obtaining age, gender, and impedance factor ($h^2/Z$) of the subject; and
    (b) according to the age, the gender and the obtained impedance fact of the subject, calculating a cross-sectional area of core muscles of the subject by a following formula: $CM_{BIA}=a-b\times age+c\times h^2/Z+d\times Sex$, wherein $CM_{BIA}$ is a cross-sectional area of core muscles measured by a bioelectrical impedance analysis, and a–d in a calculation formula are regression coefficients in a regression analysis.

2. The method of evaluating core muscles by bioimpedance technology as claimed in claim 1, wherein said core muscles are one or all of psoas major, quadratus lumborum, erector spinae, and abdominal muscles.

3. The method of evaluating core muscles by bioimpedance technology as claimed in claim 1, wherein when said core muscles are abdominal muscles, a formula of said core muscles is $AM_{BIA}=CM_{BIA}-PM_{BIA}-QM_{BIA}-ES_{BIA}$, wherein $AM_{BIA}$, $CM_{BIA}$, $PM_{BIA}$, $QM_{BIA}$, $ES_{BIA}$ are cross-sectional areas of abdominal muscles, core muscles, psoas major and quadratus muscle measured by the bioelectrical impedance analysis.

* * * * *